United States Patent
Gaylord et al.

(10) Patent No.: US 11,607,330 B1
(45) Date of Patent: Mar. 21, 2023

(54) ORTHOPEDIC AND ORTHOTIC BRACE AND HINGE ASSEMBLY WITH CUSTOM-SELECTABLE RANGE-CONTROLLING HINGE STOPS

(71) Applicant: Medical Specialties, Inc., Charlotte, NC (US)

(72) Inventors: Eric Lee Gaylord, Weddington, NC (US); Joseph Robert Perry, Jr., Polkton, NC (US)

(73) Assignee: Medical Specialties, Inc., Charlotte, NC (US)

( * ) Notice: Subject to any disclaimer, the term of this patent is extended or adjusted under 35 U.S.C. 154(b) by 190 days.

(21) Appl. No.: 16/748,116

(22) Filed: Jan. 21, 2020

Related U.S. Application Data

(60) Provisional application No. 62/794,854, filed on Jan. 21, 2019.

(51) Int. Cl.
*A61F 5/01* (2006.01)

(52) U.S. Cl.
CPC ............ *A61F 5/0102* (2013.01); *A61F 5/013* (2013.01); *A61F 5/0123* (2013.01); *A61F 2005/0139* (2013.01); *A61F 2005/0167* (2013.01); *A61F 2005/0179* (2013.01)

(58) Field of Classification Search
CPC .... A61F 5/0102; A61F 5/0123; A61F 5/0125; A61F 5/013; A61F 2005/0137; A61F 2005/0139; A61F 2005/0165; A61F 2005/0167; A61F 2005/0179; A61F 2005/0132–0181
USPC .......................................................... 602/16
See application file for complete search history.

(56) References Cited

U.S. PATENT DOCUMENTS

| | | | |
|---|---|---|---|
| 4,732,143 A * | 3/1988 | Kausek | A61F 5/0123 602/16 |
| 5,038,765 A | 8/1991 | Young et al. | |
| 5,443,444 A | 8/1995 | Pruyssers | |
| 2004/0049140 A1 | 3/2004 | Doty et al. | |
| 2012/0302932 A1* | 11/2012 | Ferrigolo | A61F 5/0123 602/16 |
| 2017/0340471 A1* | 11/2017 | Mason | A61F 5/0123 |
| 2020/0182287 A1* | 6/2020 | Heronen | A61F 5/0102 |

OTHER PUBLICATIONS

"Stair-step", Collins English Dictionary, 2022 (Year: 2022).*

* cited by examiner

*Primary Examiner* — Rachael E Bredefeld
*Assistant Examiner* — Trisha Talapatra
(74) *Attorney, Agent, or Firm* — Schwartz Law Firm, P.C.

(57) ABSTRACT

A brace incorporates an elongated strut having rigid hinge bars interconnected by an adjustable dual-axis ROM hinge. An exchangeable hinge stop is removably positioned within the ROM hinge, and designed to engage the hinge bars at a predetermined flexion/extension limit, thereby restricting pivoting movement of the strut and custom limiting a range of extension or flexion of the body part. A stop retention post cooperates with a flex member to hold the hinge stop in position relative to the first and second hinge bars. Lifting the flex member outwardly away from the hinge plate allows the hinge stop to be removed from the ROM hinge and exchanged.

18 Claims, 12 Drawing Sheets

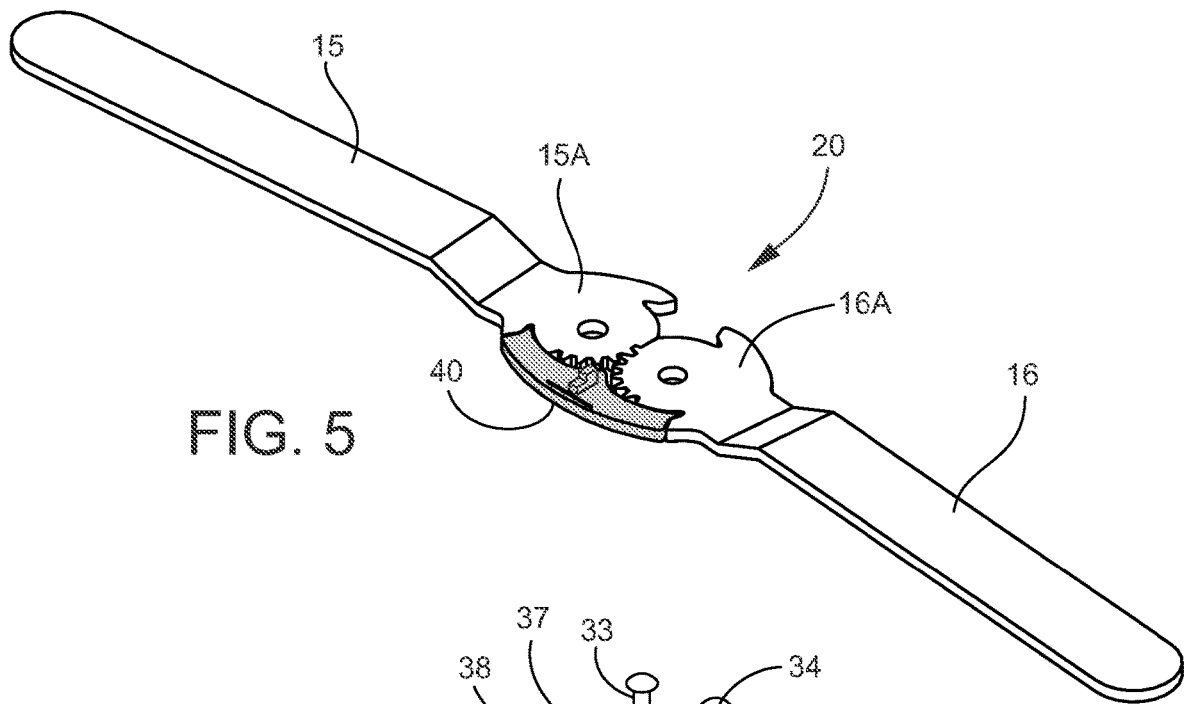
FIG. 5
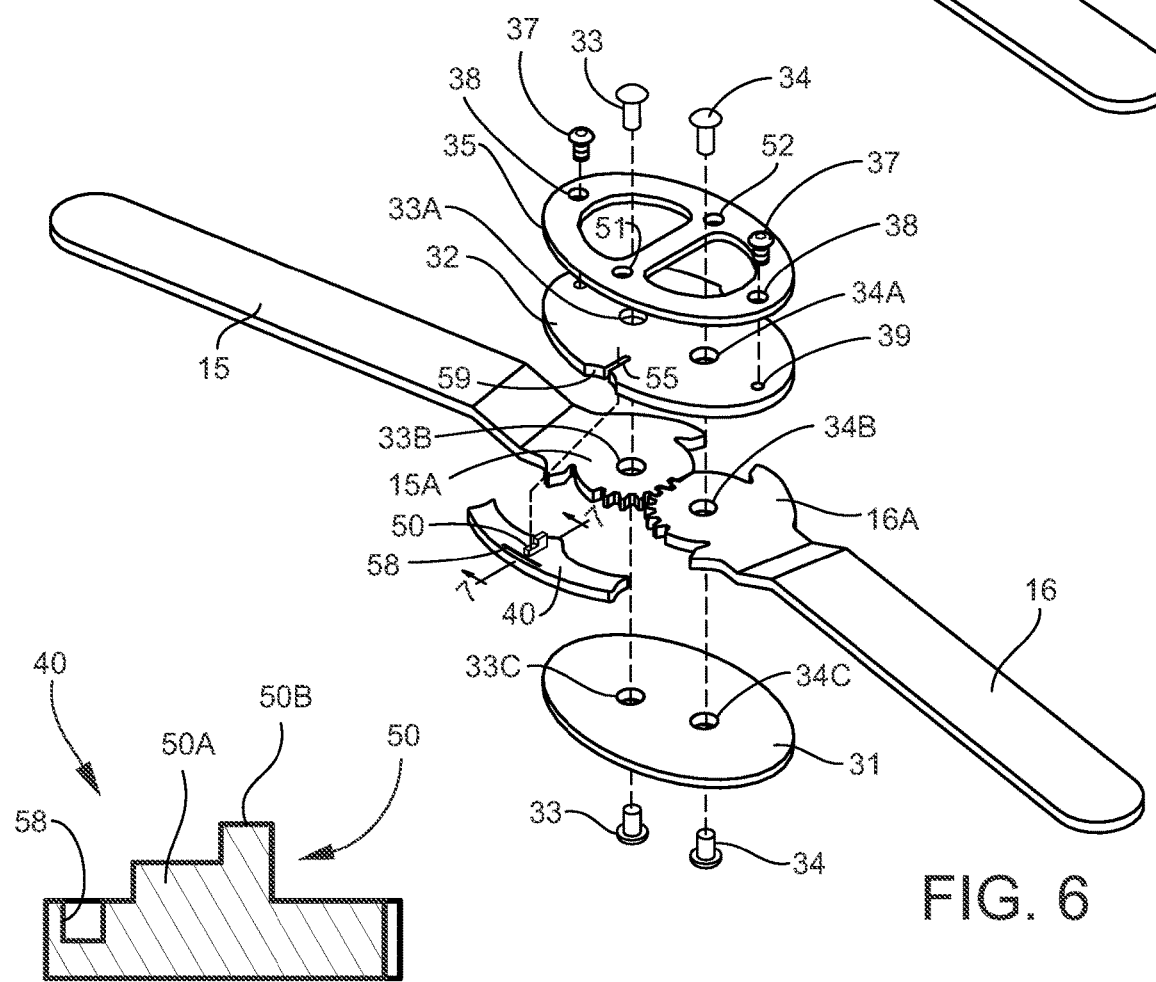
FIG. 7
FIG. 6

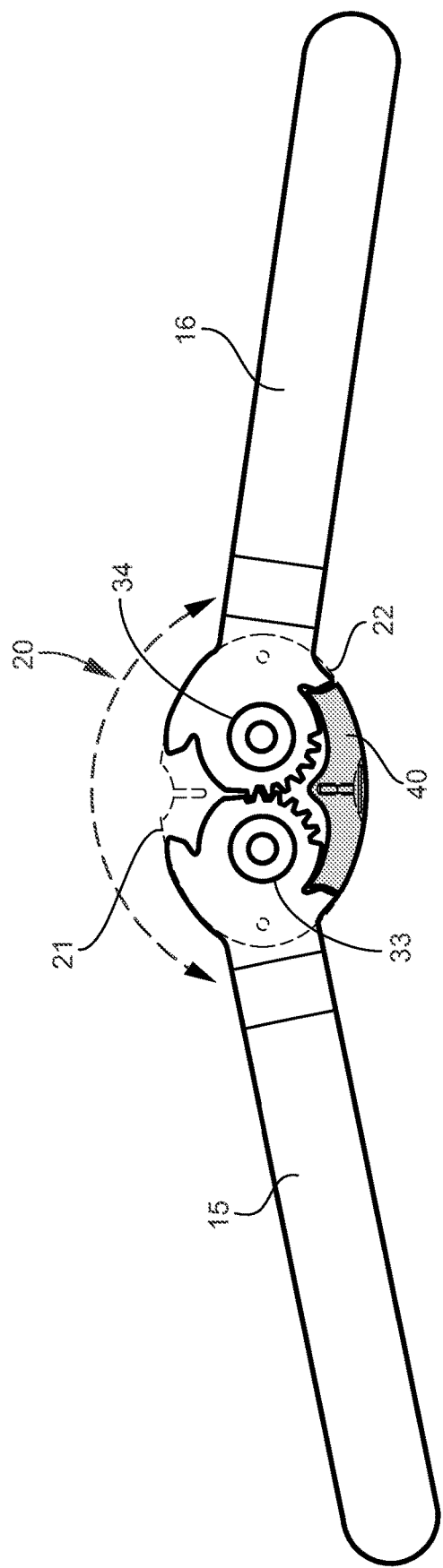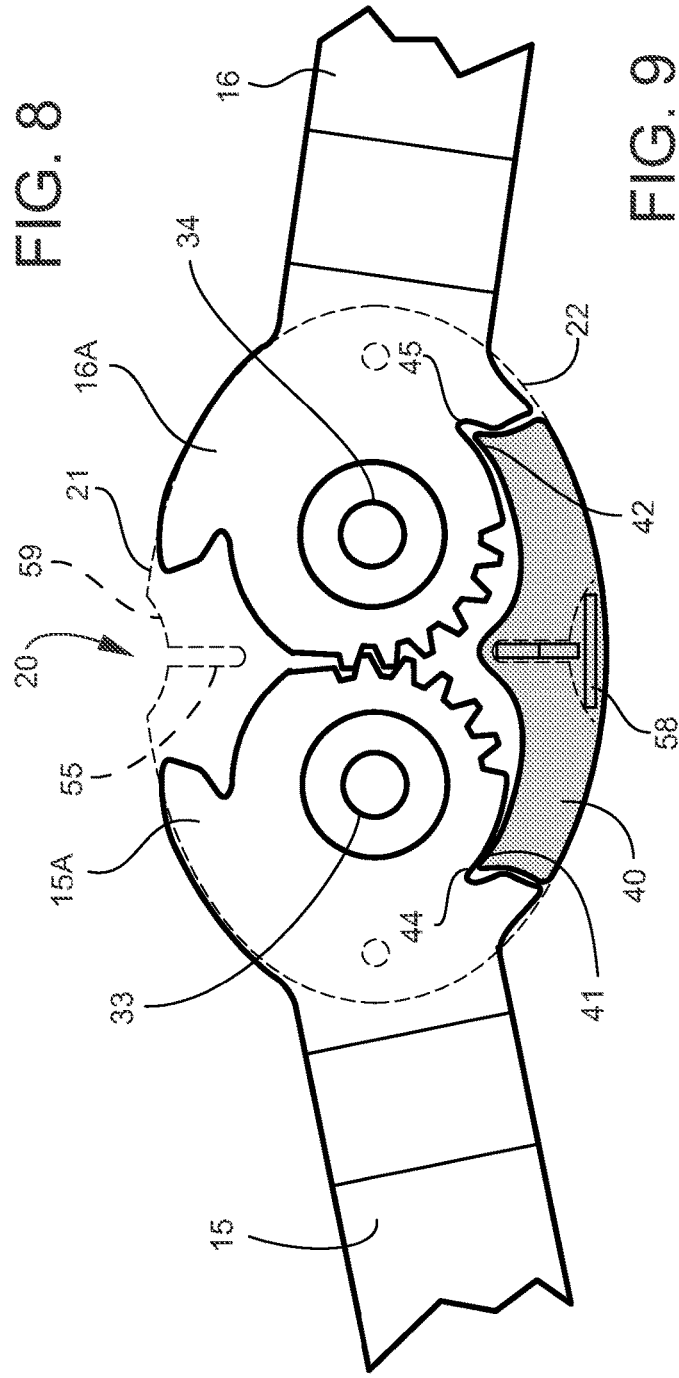

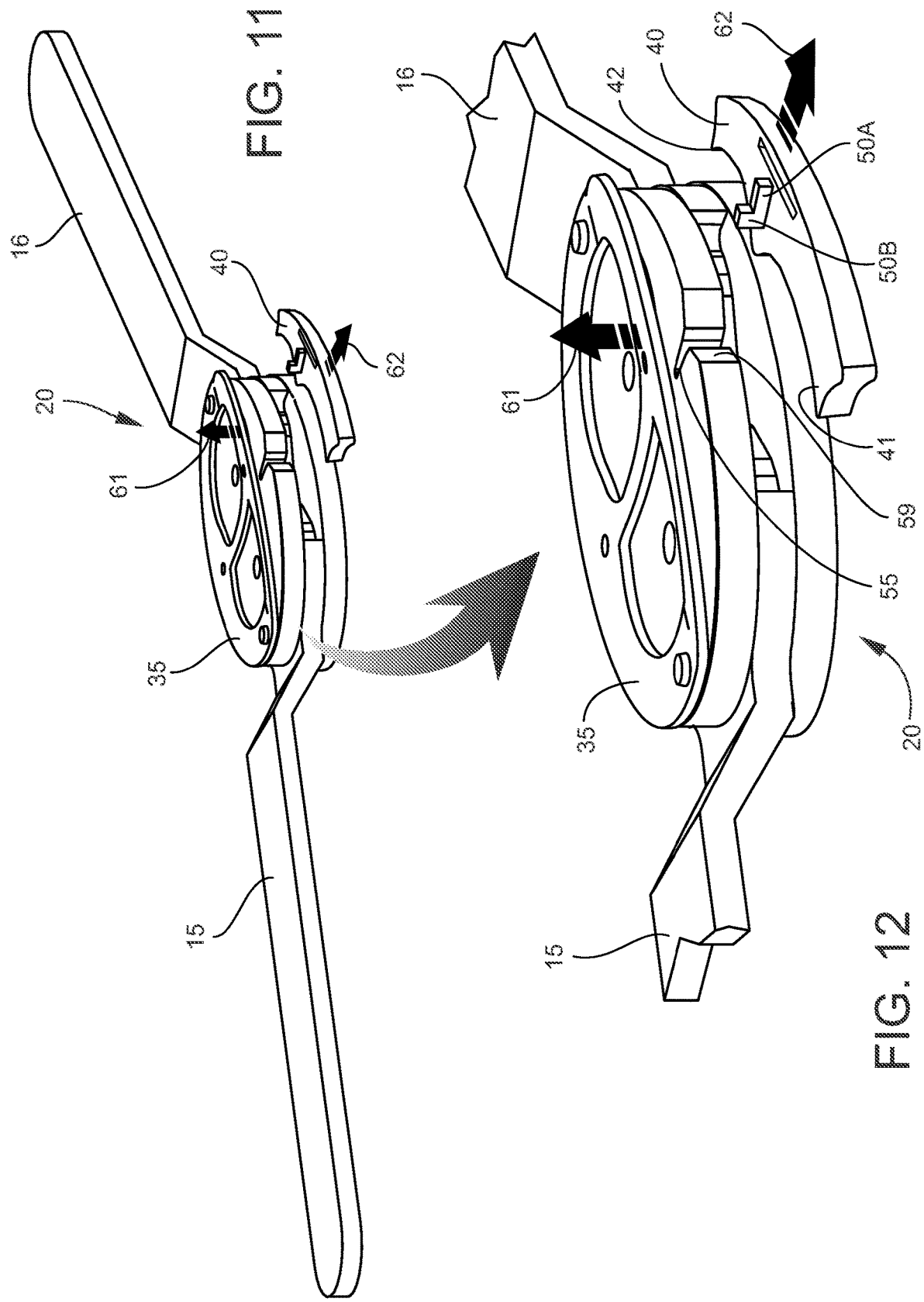

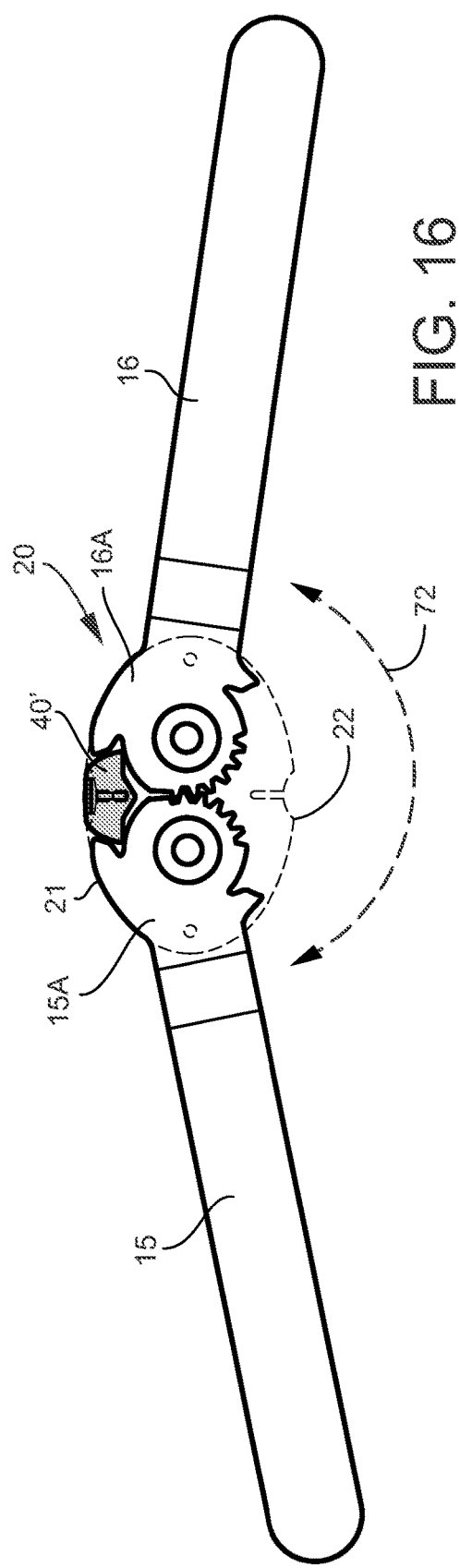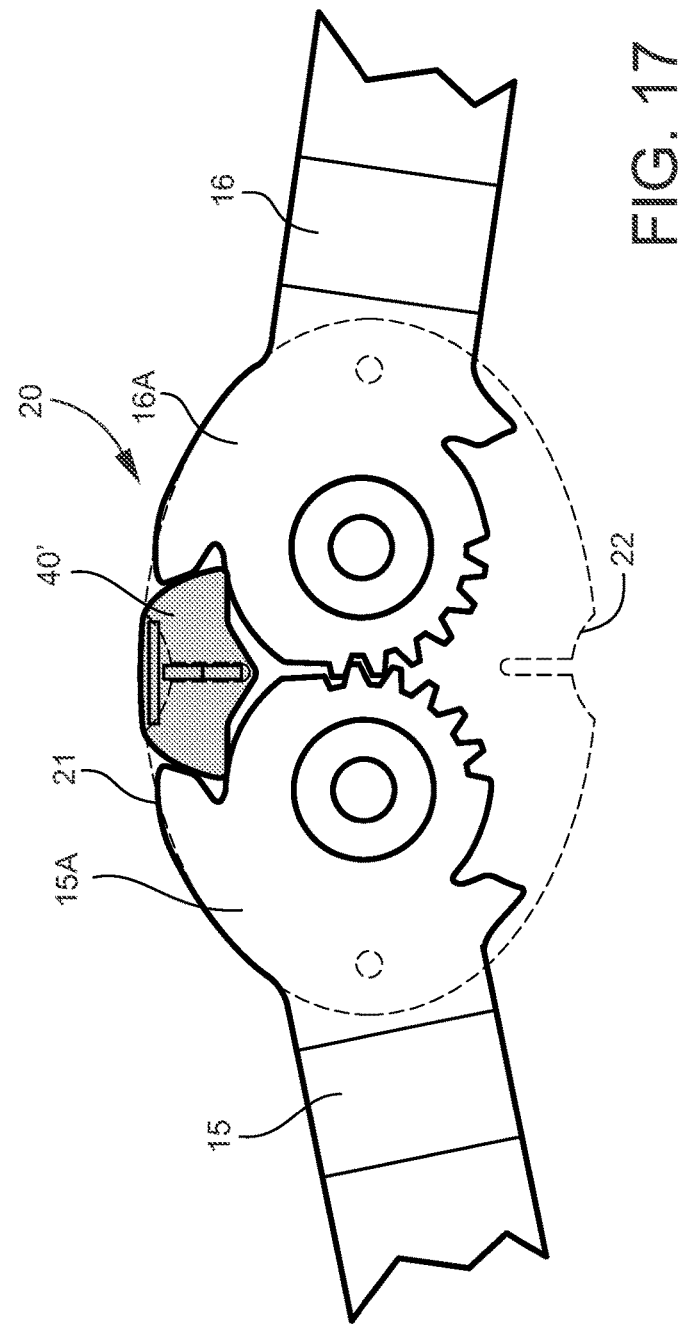

ORTHOPEDIC AND ORTHOTIC BRACE AND HINGE ASSEMBLY WITH CUSTOM-SELECTABLE RANGE-CONTROLLING HINGE STOPS

TECHNICAL FIELD AND BACKGROUND OF THE DISCLOSURE

The present disclosure relates broadly and generally to an orthopedic and orthotic brace and hinge assembly with custom-selectable range-controlling hinge stops. As an orthopedic device, the present disclosure may function to prevent or manage musculoskeletal problems, while as an orthotic the device of the present disclosure may function to support or straighten weak joints or limbs.

In exemplary embodiments, the present knee brace incorporates custom-selectable range-controlling hinge stops which allow the physician or practitioner to independently adjust and subsequently change the degree to which the patient's knee will flex and extend. The exemplary brace is designed to stabilize and control mild to moderate levels of medial/lateral movement, and may be used for indications including osteoarthrosis, tear of medial meniscus or ACL, rheumatoid arthritis, mild to severe ligament instabilities, closed fracture of patella, meniscal cartilage derangement, knee sprains and strains, and others.

Dual axis, geared, ROM hinge assemblies for orthopedic and orthotic devices are known in the art. Some prior art hinge assemblies utilize extractable inserts or "stops" designed to control the angular movement or range-of-motion of the hinge elements. These extractable inserts are commonly removably affixed to the hinge assembly using small screws or other hardware requiring the use of special tools, wrenches or screwdrivers.

SUMMARY OF EXEMPLARY EMBODIMENTS

Various exemplary embodiments of the present disclosure are described below. Use of the term "exemplary" means illustrative or by way of example only, and any reference herein to "the invention" is not intended to restrict or limit the invention to exact features or steps of any one or more of the exemplary embodiments disclosed in the present specification. References to "exemplary embodiment," "one embodiment," "an embodiment," "various embodiments," and the like, may indicate that the embodiment(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may.

It is also noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

According to one exemplary embodiment, the present disclosure comprises a brace adapted for being applied to a body part of a wearer. The exemplary brace may be particularly designed for the knee, elbow or other body part/joint. The brace includes an elongated strut with first and second rigid hinge bars. Each hinge bar has a proximal end and a distal end. An adjustable dual-axis ROM hinge pivotably interconnects the proximal ends of the first and second hinge bars at respective spaced apart pivot points. The ROM hinge has a flexion side and an extension side. The exemplary ROM hinge comprises a hinge plate, first and second pivot fasteners, and a resilient flex member. The hinge plate resides adjacent the proximal ends of the hinge bars, and first and second spaced apart pivot fasteners secure the hinge bars to the hinge plate at respective pivot points. An exchangeable, extractable hinge stop is located on a selected one of the flexion and extension sides of the ROM hinge adjacent the proximal ends of the first and second hinge bars and between the hinge plate and the flex member. The hinge stop is designed to engage the hinge bars at a predetermined flexion/extension limit, thereby restricting pivoting movement of the strut and custom limiting a range of extension or flexion of the body part. A stop retention post cooperates with the flex member to hold the hinge stop in position relative to the first and second hinge bars. Lifting the flex member outwardly away from the hinge plate allows the hinge stop to be removed from the ROM hinge and exchanged.

In other exemplary embodiments, the present ROM hinge may incorporate 2 or more exchangeable range-controlling stops on both the flexion and extension sides of the hinge. For example, cooperating stops may be inserted on both sides of the ROM hinge to create a "drop lock" (or straight leg) immobilizer with substantially zero-degree (0°) flexion and extension limits. In other embodiments, the exemplary brace may omit a range-controlling stop such that the brace enables a full range of unrestricted extension and flexion movement.

A flexible wraparound strap closure may be included to secure and position the strut on the body part of the wearer. Alternatively, the exemplary brace may be temporarily applied to the body part using athletic tape, wraps or other means.

According to another exemplary embodiment, the proximal ends of the first and second hinge bars comprise a plurality of intermeshing gear teeth.

According to another exemplary embodiment, the proximal ends of the first and second hinge bars further comprise respective stop surfaces (directly) adjacent leading ones of the plurality of gear teeth. The stop surfaces cooperate to restrict hyperextension of the strut.

According to another exemplary embodiment, the hinge stop is located on the extension side of the ROM hinge and is configured to limit pivoting movement of the strut, such that a range of extension of the body part is restricted at an extension angle between 10-degrees and 60-degrees.

According to another exemplary embodiment, the hinge stop is located on the flexion side of the ROM hinge and is configured to limit pivoting movement of the strut, such that a range of flexion of the body part is restricted at a flexion angle between 10-degrees and 90-degrees.

According to another exemplary embodiment, and comprising a second hinge plate adjacent the resilient flex member and cooperating with the first hinge plate to sandwich the proximal ends of the hinge bars therebetween.

According to another exemplary embodiment, the stop retention post has a stair-step shape comprising integrally formed short and tall portions. In other embodiments, the retention post may comprise any other structure or protrusion of any shape, size or formation which extends outwardly from a major planar surface of the stop.

According to another exemplary embodiment, the hinge stop comprises a surface fingernail groove designed to facilitate removal of the hinge stop from the ROM hinge.

According to another exemplary embodiment, the proximal ends of the first and second hinge bars define respective stop notches, and wherein the hinge stop comprise opposing integrally formed end tongues designed to insert into respective stop notches at the predetermined flexion/extension limit.

In another exemplary embodiment, the present brace comprises an elongated strut extending between opposite ends of the brace and including first and second rigid hinge bars. Each hinge bar has a proximal end and a distal end. An adjustable dual-axis ROM hinge pivotably interconnects the proximal ends of the first and second hinge bars at respective spaced apart pivot points. The ROM hinge has a flexion side and an extension side. The exemplary ROM hinge comprises a hinge plate, first and second spaced apart pivot fasteners, and a flex member. The hinge plate resides adjacent the proximal ends of the first and second hinge bars, and first and second spaced apart pivot fasteners secure the hinge bars to the hinge plate at respective pivot points. An exchangeable hinge stop is located on a selected one of the flexion and extension sides of the ROM hinge adjacent the proximal ends of the first and second hinge bars and between the hinge plate and the flex member. The hinge stop is designed to engage the hinge bars at a predetermined flexion/extension limit, thereby restricting pivoting movement of the strut and custom limiting a range of extension or flexion of the body part. A stop retention post cooperates with the flex member to hold the hinge stop in position relative to the first and second hinge bars. Lifting the flex member outwardly away from the hinge plate allows the hinge stop to be removed from the ROM hinge and exchanged.

In yet another exemplary embodiment, the present brace comprises an elongated strut extending between opposite ends of the brace and including first and second rigid hinge bars. Each hinge bar has a proximal end and a distal end. An adjustable dual-axis ROM hinge pivotably interconnects the proximal ends of the first and second hinge bars at respective spaced apart pivot points. The ROM hinge has a flexion side and an extension side. The exemplary ROM hinge comprises first and second hinge plates, first and second spaced apart pivot fasteners, and a resilient flex ring. The first and second hinge plates reside adjacent the first and second hinge bars, and sandwich the proximal ends of the hinge bars therebetween. The first and second pivot fasteners secure the first and second hinge bars to the first and second hinge plates at respective pivot points. The flex ring is affixed to an outside of the second hinge plate at opposite ends of the ROM hinge and is continuously unattached to the second hinge plate along the flexion and extension sides of the ROM hinge. An exchangeable hinge stop is located on a selected one of the flexion and extension sides of the ROM hinge adjacent the proximal ends of the first and second hinge bars and between the first and second hinge plates. The hinge stop is designed to engage the hinge bars at a predetermined flexion/extension limit, thereby restricting pivoting movement of the strut and custom limiting a range of extension or flexion of the body part. The hinge stop comprises a stop retention post inserted into a selected complementary post hole formed in the peripheral margin of the flex ring at the flexion or extension sides of the ROM hinge. The retention post cooperates with the flex ring to hold the hinge stop in position relative to the first and second hinge bars. Lifting the flex ring outwardly away from the second hinge plate allows the hinge stop to be removed from the ROM hinge and exchanged. A flexible strap closure functions to secure and position the strut on the body part of the wearer.

According to another exemplary embodiment, the second hinge plate has an edge slot aligned with the post hole of the flex ring for receiving the retention post of the hinge stop.

In still another exemplary embodiment, the present disclosure comprises an orthopedic and orthotic hinge assembly with custom-selectable and exchangeable range-controlling hinge stops. The exemplary hinge assembly incorporates a spring-steel ring with an inwardly protruding tooth designed to insert through a complementary slot formed with the range-controlling stop. The range-controlling stop is readily extracted from the hinge assembly by manually lifting the spring-steel ring outwardly to remove the tooth from the stop slot, thereby allowing the stop to freely release or dropout from its temporarily secured position inside the assembly. In exemplary embodiments, the hinge stop(s) can be quickly and readily exchanged using only a finger and without requiring any special tool, wrench or screw driver.

BRIEF DESCRIPTION OF THE DRAWINGS

Exemplary embodiments of the present disclosure will hereinafter be described in conjunction with the following drawing figures, wherein like numerals denote like elements, and wherein:

FIG. 5 is a further view of the exemplary brace strut in the extended condition, and with various components removed to more clearly illustrate the exchangeable hinge stop;

FIG. 6 is a perspective view of the exemplary brace strut with components of the ROM hinge exploded away;

FIG. 7 is a cross-sectional view of the exemplary hinge stop taken substantially along line 7-7 of FIG. 6;

FIGS. 8 and 9 are further views of the exemplary brace strut in the extended condition, and showing the hinge stop inserted on a flexion side of the ROM hinge;

FIGS. 10-13 are sequential views demonstrating extraction of the hinge stop from the exemplary ROM hinge;

FIGS. 16 and 17 are views of the brace strut showing an alternative smaller hinge stop positioned on the extension side of the ROM hinge;

DESCRIPTION OF EXEMPLARY EMBODIMENTS AND BEST MODE

The present invention is described more fully hereinafter with reference to the accompanying drawings, in which one or more exemplary embodiments of the invention are shown. Like numbers used herein refer to like elements throughout. This invention may, however, be embodied in many different forms and should not be construed as limited to the embodiments set forth herein; rather, these embodiments are provided so that this disclosure will be operative, enabling, and complete. Accordingly, the particular arrangements disclosed are meant to be illustrative only and not limiting as to the scope of the invention, which is to be given the full breadth of the appended claims and any and all equivalents thereof. Moreover, many embodiments, such as adaptations, variations, modifications, and equivalent arrangements, will be implicitly disclosed by the embodiments described herein and fall within the scope of the present invention.

Although specific terms are employed herein, they are used in a generic and descriptive sense only and not for purposes of limitation. Unless otherwise expressly defined herein, such terms are intended to be given their broad ordinary and customary meaning not inconsistent with that applicable in the relevant industry and without restriction to any specific embodiment hereinafter described. As used herein, the article "a" is intended to include one or more items. Where only one item is intended, the term "one", "single", or similar language is used. When used herein to join a list of items, the term "or" denotes at least one of the items, but does not exclude a plurality of items of the list.

For exemplary methods or processes of the invention, the sequence and/or arrangement of steps described herein are illustrative and not restrictive. Accordingly, it should be understood that, although steps of various processes or methods may be shown and described as being in a sequence or temporal arrangement, the steps of any such processes or methods are not limited to being carried out in any particular sequence or arrangement, absent an indication otherwise. Indeed, the steps in such processes or methods generally may be carried out in various different sequences and arrangements while still falling within the scope of the present invention.

Additionally, any references to advantages, benefits, unexpected results, or operability of the present invention are not intended as an affirmation that the invention has been previously reduced to practice or that any testing has been performed. Likewise, unless stated otherwise, use of verbs in the past tense (present perfect or preterit) is not intended to indicate or imply that the invention has been previously reduced to practice or that any testing has been performed.

Figure 1:
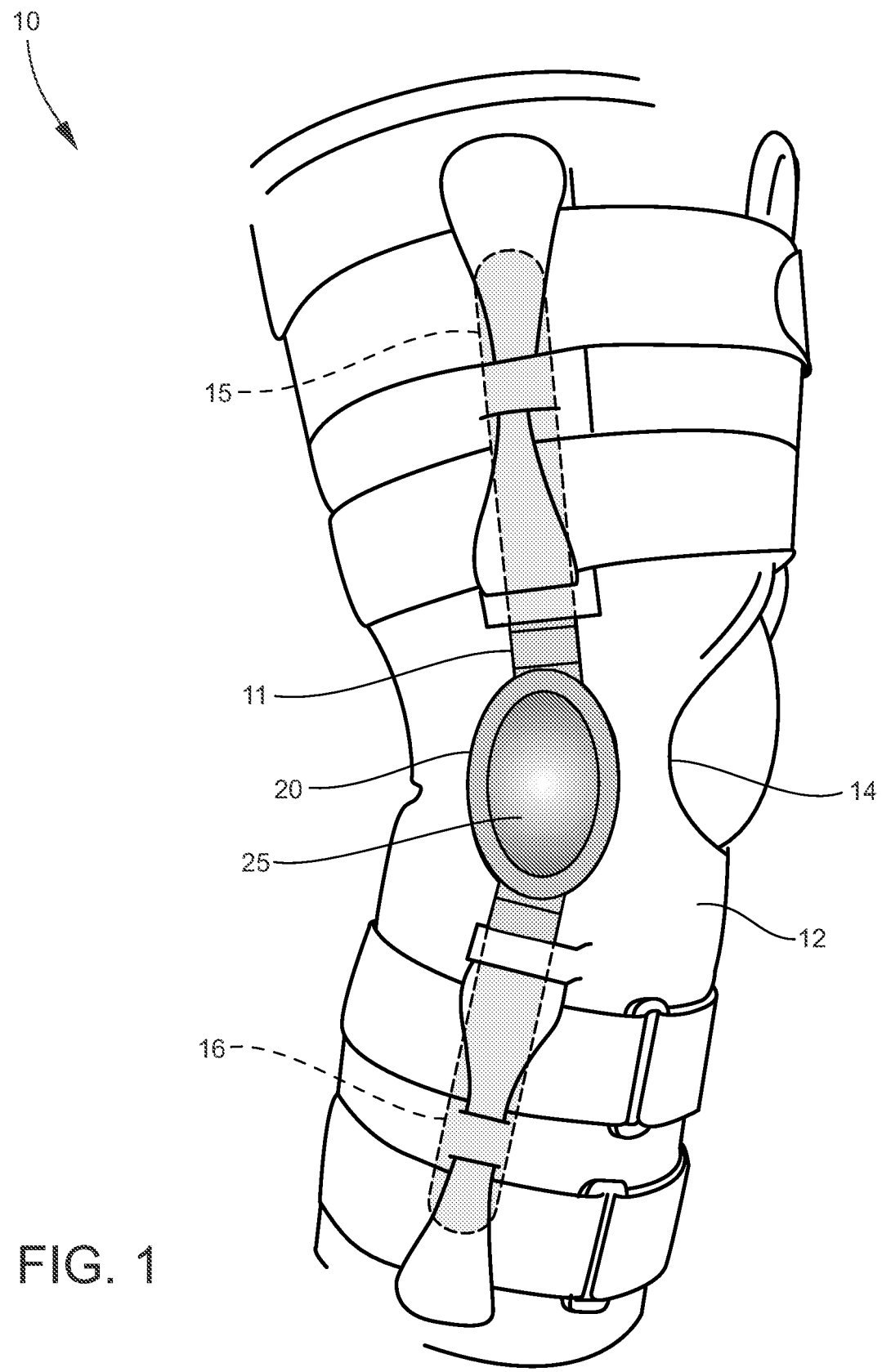
FIG. 1 is a perspective view of an orthopedic and orthotic brace according to one exemplary embodiment of the present disclosure.

Referring now specifically to the drawings, an orthopedic and orthotic knee brace according to one exemplary embodiment of the present disclosure is illustrated in FIG. 1 and shown generally at broad reference numeral 10. The exemplary knee brace 10 incorporates an elongated metal (e.g., titanium or aluminum) strut 11 integrated in a one-piece wraparound fabric body 12 adapted for being conveniently, adjustably and comfortably applied to the leg of a wearer. The wraparound body 12 has a bilateral design extending from the thigh to the calf of the wearer, and defining an open popliteal 14 constructed to minimize material bunching during flexion of the leg. The exemplary fabric may comprise a neoprene material with complementary areas hook and loop fasteners and/or one or more nylon closure straps or other conventional closure means known in the art. Other more breathable materials, such as mesh-like spacer fabric, may be incorporated in the exemplary brace. The wraparound body 12 may also include one or more inside patches of silicone gel located to reside against the skin in an area of the calf and functioning to restrict/limit the brace from migrating distally during use. The exemplary metal strut 11 is held within and adjacent nylon-reinforced fabric sleeves formed in the wraparound body 12 of the brace 10.

Figure 2:
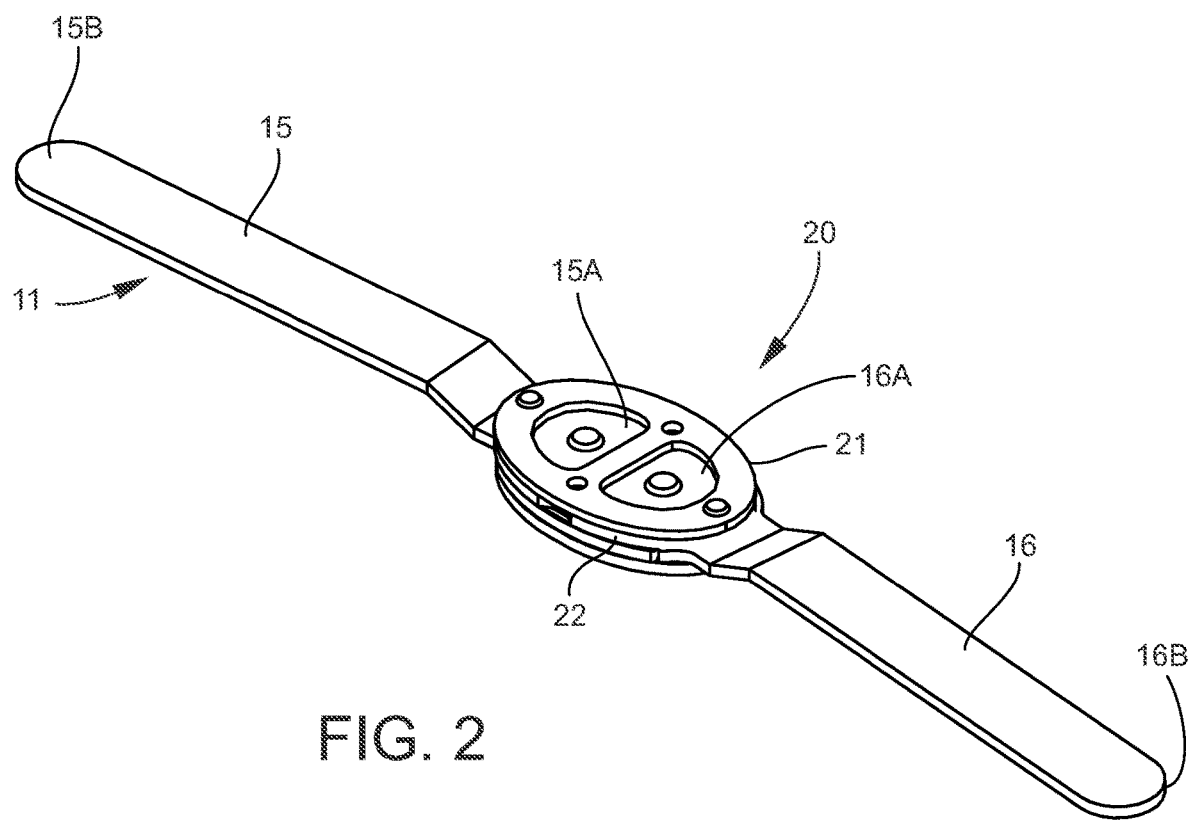
FIG. 2 is a perspective view of an exemplary strut incorporated in the present knee brace, and comprising pivotably interconnected hinge bars and an adjustable ROM hinge.
Figure 3:
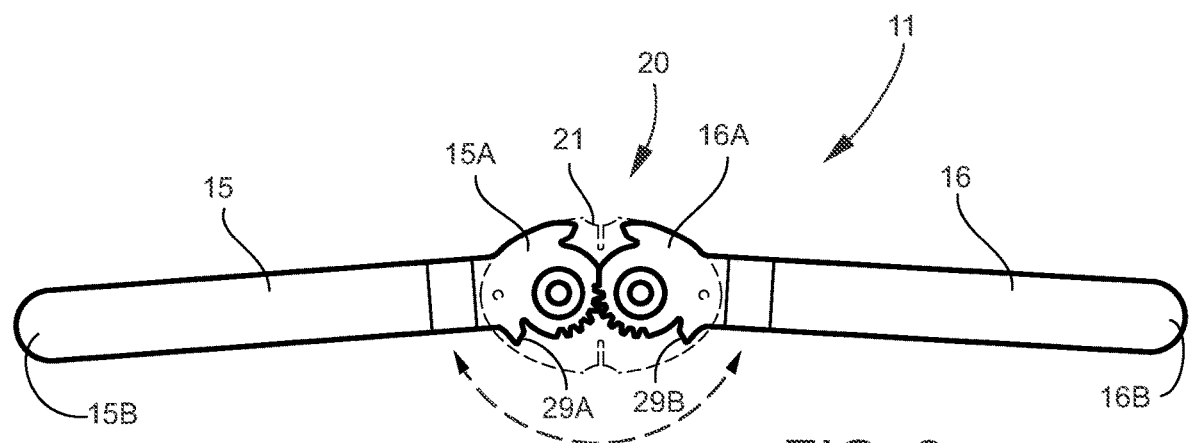
FIGS. 3 and 4 are views of the brace strut in extended and fully pivoted conditions.
Figure 4:
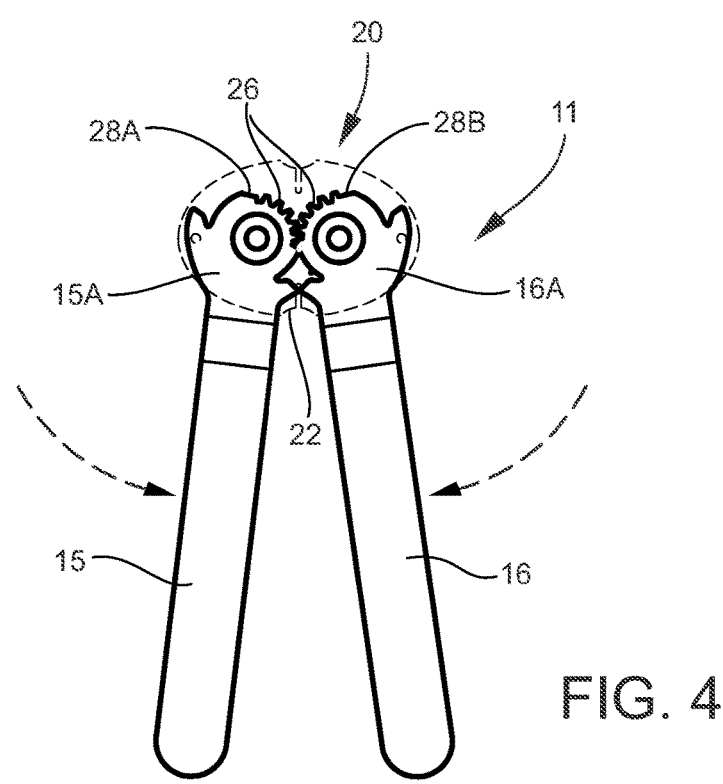
Figure 10:
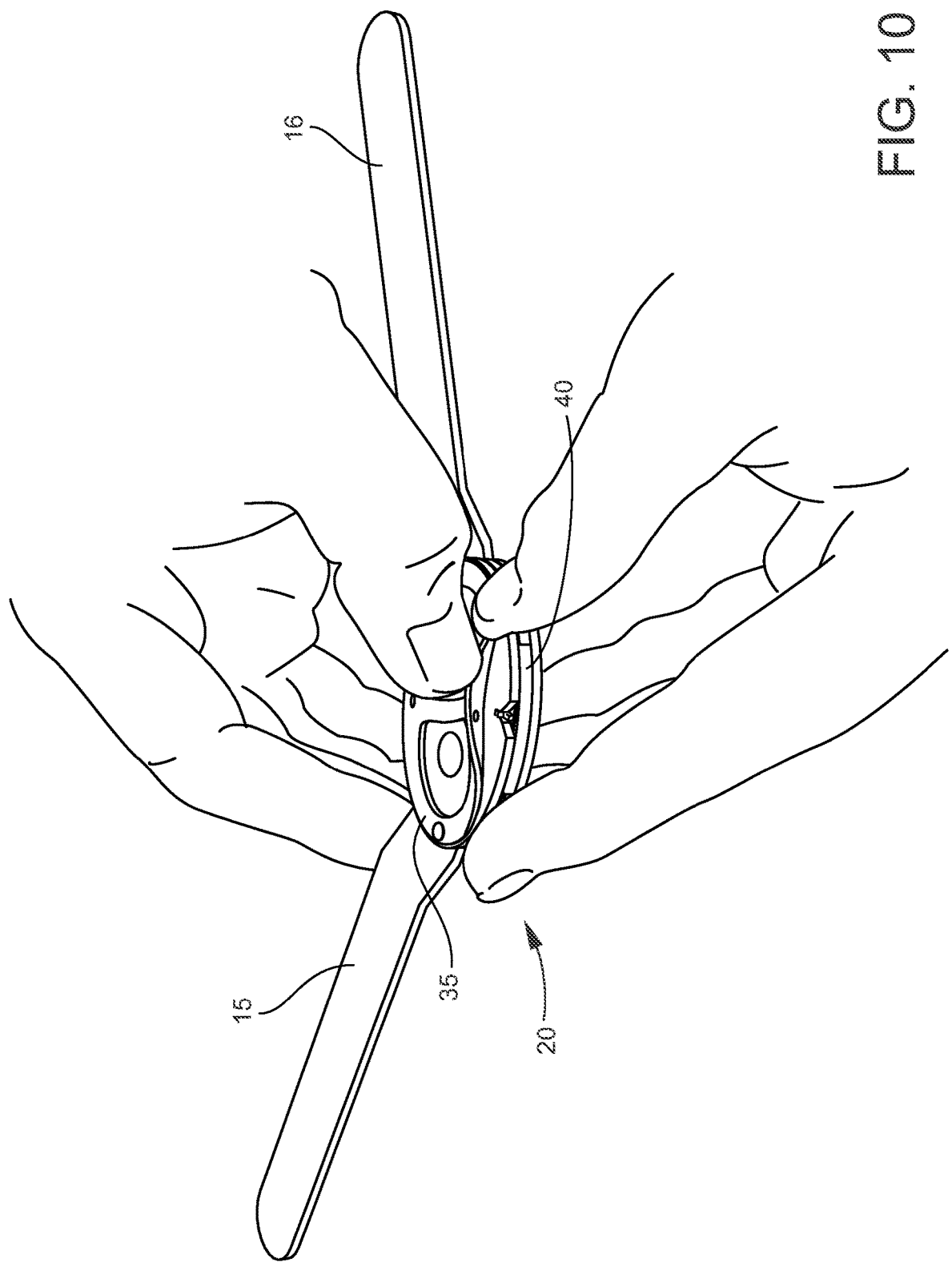

Referring to FIGS. 1-4, the metal strut 11 extends between opposite ends of the brace 10 and incorporates first and second rigid flat hinge bars 15, 16 operatively interconnected by an adjustable dual-axis ROM hinge 20. The ROM hinge 20 has extension and flexion sides 21, 22, and when unrestricted allows a maximum range of motion from 0-degrees [full extension of the leg] to 100-degrees [full flexion of the leg]. In one embodiment, the hinge arms 15, 16 are ergonomically bent adjacent the ROM hinge 20, as best shown in FIG. 2, to space an inside or "body-side" the ROM hinge 20 from the knee joint. A rounded oval shaped cover 25 shown in FIG. 1 may be applied to the exposed outside of the ROM hinge 20.

Each of the hinge bars 15, 16 has a proximal end 15A, 16A and a distal end 15B, 16B. The proximal ends 15A, 16A have a plurality of intermeshing gear teeth 26, best shown in FIGS. 3 and 4, and respective stop surfaces 28A, 28B and 29A, 29B formed directly adjacent leading ends of the gear teeth 26 on the extension side 21 of ROM hinge 20 and proximate trailing ends of the gear teeth 26 on the flexion side 22 of ROM hinge 20. When engaging, the stop surfaces 28A, 28B cooperate to prevent hyperextension of the strut 11—i.e., movement beyond 0-degree extension. Stop surfaces 29A, 29B function to limit pivoting of the strut 11 in an opposition direction, thereby limiting maximum flexion of the leg at a predetermined angle (e.g., 100-degrees).

Referring to FIGS. 5-9, The exemplary ROM hinge 20 includes first and second flat metal hinge plates 31, 32, first and second spaced apart pivot fasteners 33, 34, and a resilient polycarbonate flex ring 35. The hinge bars 15, 16 of strut 11 are sandwiched between the hinge plates 31, 32 at respective proximal ends 15A, 16A, and are pivotably joined together by the pivot fasteners 33, 34 at spaced-apart pivot points. As shown in FIG. 6, the exemplary pivot fasteners 33, 34 extend through aligned holes 33A, 33B, 33C and 34A, 34B, 34C and may comprise standard double-neck metal rivets or other suitable hardware. Thin polymer washers (not shown) may be located between the hinge plates 31, 32 and hinge bars 15, 16 to reduce friction and abrasion between the mating metal surfaces. Such washers may be fabricated of a polyoxymethylene material or other high-performance friction/abrasion resistant thermoplastic.

The resilient flex ring 35 is affixed to an outside of the second hinge plate 32 at opposite ends of the ROM hinge 20 and is continuously unattached to the second hinge plate 32 along the extension and flexion sides 21, 22 of the ROM hinge 20. The flex ring 35 may be attached using small threaded screws 37 inserted through ring holes 38 and into internally-threaded holes 39 of the hinge plate 32. In alternative embodiments, the exemplary brace 10 may incorporate any other resilient and flexible member which may function as described further below in a manner comparable to the flex ring 35. The flex member may be fabricated of a spring steel or other flexible/resilient polymeric material.

An exchangeable hinge stop 40 is located on a selected one of the extension and flexion sides 21, 22 of the ROM hinge 20 adjacent the proximal ends 15A, 16A of the hinge bars 15, 16 and between the hinge plates 31, 32. The hinge stop 40 is designed to engage the interconnected hinge bars 15, 16 at a predetermined flexion/extension limit, thereby restricting pivoting movement of the strut 11 and custom-limiting a range of extension or flexion of the body part. In the example of FIGS. 5-9, the hinge stop 40 is located on the flexion side 22 of the ROM hinge 20 and functions to limit pivoting movement of the strut 11 to a prescribed degree—e.g., 10-degrees. This restricts movement of the leg within a 10-degree range of motion.

As best shown in FIG. 9, the exemplary hinge stop 40 has opposing integrally formed end tongues 41, 42 designed to insert into complementary stop notches 44, 45 formed in respective proximal ends 15A, 16A of hinge bars 15, 16. The end tongues 41, 42 insert into the stop notches 44, 45 of hinge bars 15, 16 when the brace strut 11 is urged by the wearer against the prescribed 10-degree flexion limit. Engaging surfaces of the end tongues 41, 42 and stop notches 44, 45 cooperate to prevent the hinge stop 40 from unintentionally dislodging from the ROM hinge 20.

Referring to FIGS. 6 and 7, the exemplary hinge stop 40 may further comprise an outward-projecting stop retention post 50 designed for inserting into a selected one of complementary post holes 51, 52 formed in the peripheral margin of the flex ring 35 at the extension and flexion sides 21, 22 of the ROM hinge 20. The retention post 50 has a generally stair-step shape comprising integrally formed short and tall portions 50A, 50B. The height of the short portion 50A corresponds substantially to the thickness of hinge plate 32, while the tall portion 50B is designed to extend beyond the hinge plate 32 and into the selected post hole 51, 52 of flex ring 35. Opposing edge slots 55 formed with the hinge plate 32 are aligned with respective post holes 51, 52 of flex ring 35 and serve to facilitate proper insertion of the hinge stop 40 into the ROM hinge 20. The retention post 50 cooperates with the flex ring 35 to further hold the hinge stop 40 in position relative to the first and second hinge bars 15, 16 of strut 11. As discussed further below, lifting the flex ring 35 outwardly away from the second hinge plate 32 allows the hinge stop 40 to be removed from the ROM hinge 20 and either repositioned on an opposite flexion/extension side of the ROM hinge 20 or exchanged with an different size hinge stop. A fingernail groove 58 may be formed in the post-side surface of hinge stop 40 to facilitate removal of the hinge stop 40 from the ROM hinge 20.

Figure 13:
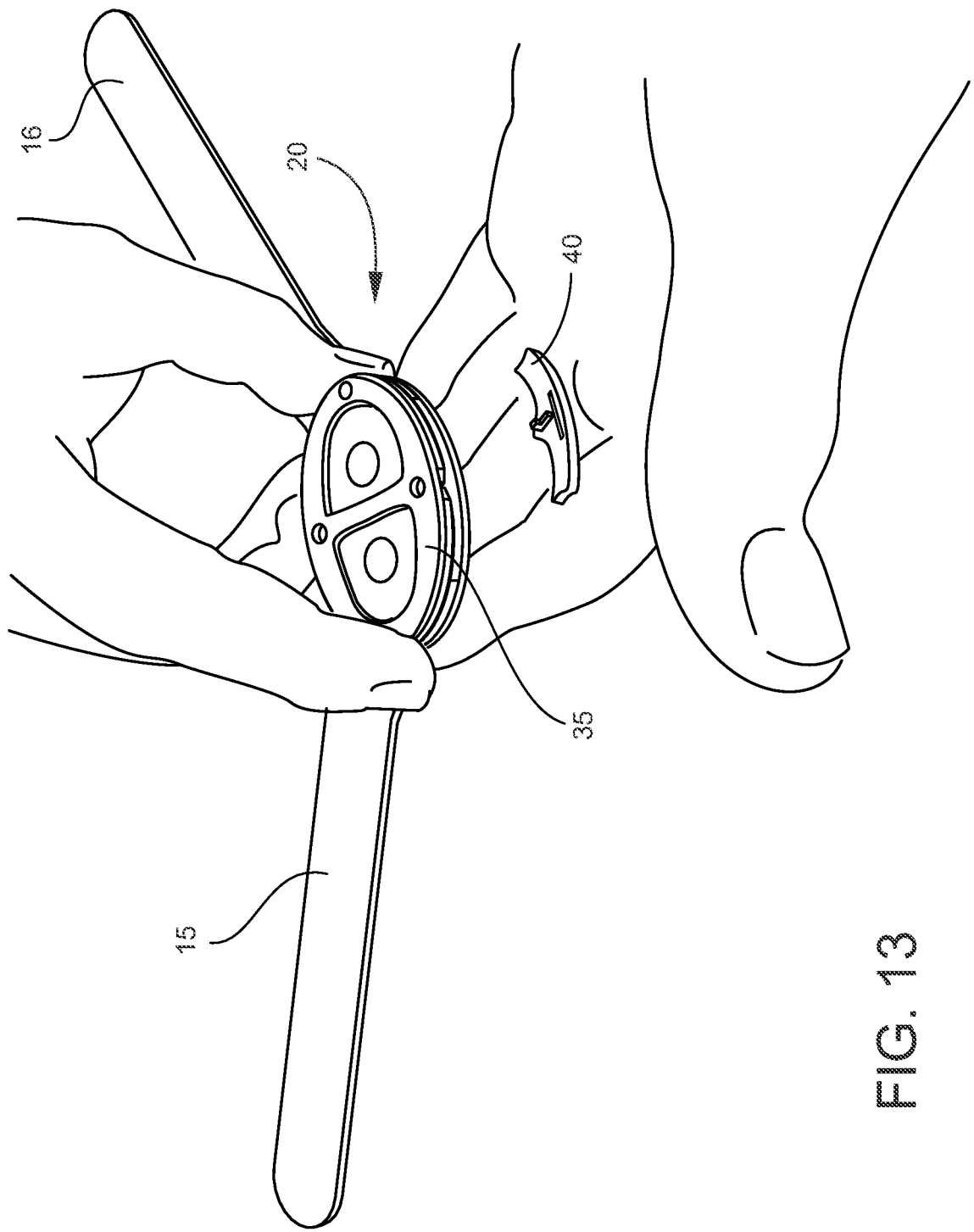

As demonstrated in FIGS. 10-13, the hinge stop 40 is removed from the ROM hinge 20 (e.g., by a physician or practitioner) by lifting the flex ring 35 outwardly away from the hinge plate 32 a sufficient degree to allow the stop post 50 to clear the post hole 51. The hinge plate 32 may have opposing recessed edges 59 located at the edge slots 55 for allowing the thumb to more readily engage and lift the flex ring 35, as shown in FIG. 8. With the flex ring 35 lifted, the fingernail groove 58 may be used to help dislodge the hinge stop 40 from the ROM hinge 20. See direction arrows 61, 62 in FIGS. 11 and 12. The hinge stop 40 is then dropped into the palm of the hand, as shown in FIG. 13. The hinge stop 40 can be re-inserted into the ROM hinge 20 at either the extension or flexion side 21, 22 in a reverse manner.

As mentioned previously, the exemplary knee brace 10 may utilize removable and exchangeable hinges stops 40 of multiple different sizes and designs—each effecting a prescribed extension and/or flexion restriction. For example, the hinge stops may be formed in 4 distinct shapes and sizes; e.g., Stops A, B, C, and D. In the discussion below, a 0-degree angle represents a fully extended straight leg condition of the wearer. A fully flexed-leg condition comprises an angle of 100-degrees—this being an approximate angle of the lower leg below the knee relative to the upper leg above the knee.

Stop "A" when inserted on the extension side of the ROM hinge may restrict extension of the leg at 10-degrees while allowing unrestricted flexion. Stop "B" when inserted on the extension side of the ROM hinge may restrict extension of the leg at 20-degrees while allowing unrestricted flexion. Stop "C" when inserted on the extension side of the ROM hinge may restrict extension of the leg at 30-degrees while allowing unrestricted flexion. Stop "D" when inserted on the extension side of the ROM hinge may restrict extension of the leg at 40-degrees while allowing unrestricted flexion.

Stop "A" when inserted on the flexion side of the ROM hinge may restrict flexion of the leg at 90-degrees, while allowing unrestricted extension. Stop "B" when inserted on the flexion side of the ROM hinge may restrict flexion of the leg at 80-degrees, while allowing unrestricted extension. Stop "C" when inserted on the flexion side of the ROM hinge may restrict flexion of the leg at 70-degrees, while allowing unrestricted extension. Stop "D" when inserted on the flexion side of the ROM hinge may restrict flexion of the leg at 60-degrees, while allowing unrestricted extension.

Figure 14:
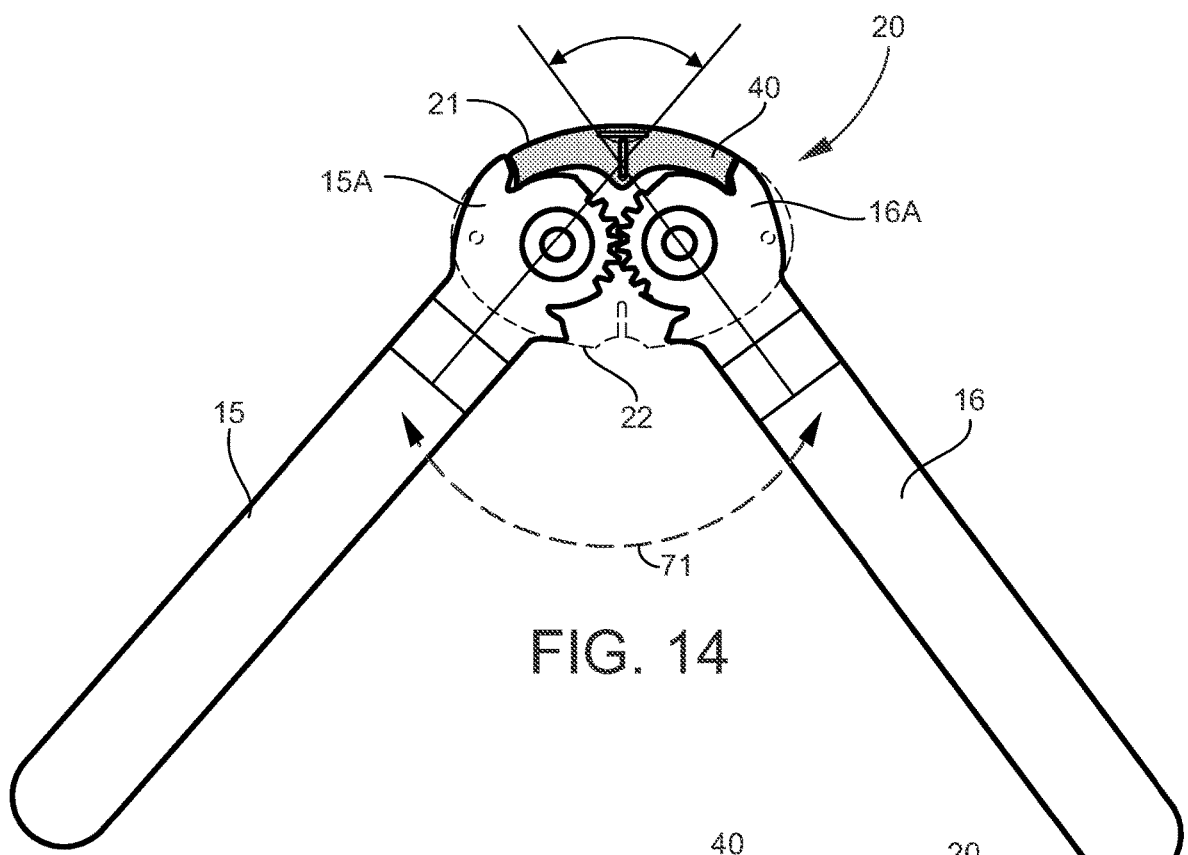
FIGS. 14 and 15 are views of the brace strut showing the hinge stop re-positioned on the extension side of the ROM hinge.
Figure 15:
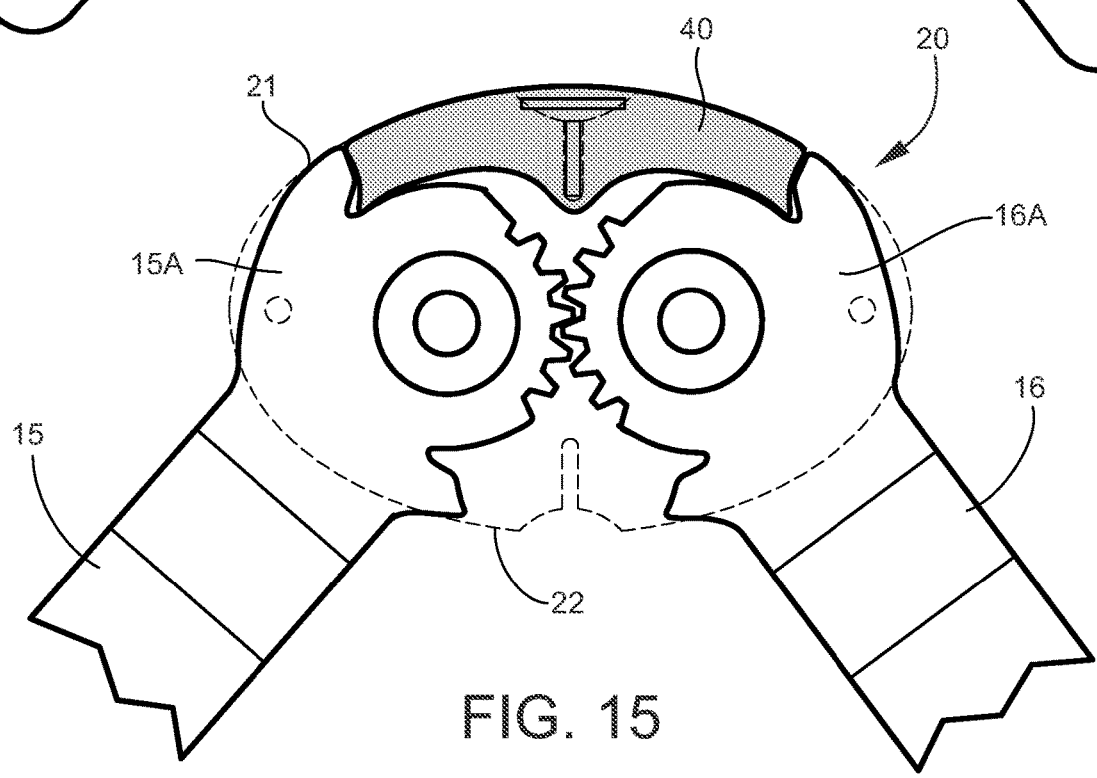

FIGS. 14 and 15 show the hinge stop 40 described above located on the extension side 21 of ROM hinge 20 between proximal ends 15A, 16A of the hinge bars 15, 16. In this position, the hinge bars 15, 16 can freely pivot within a range of motion indicated by arrow 71.

Figure 18:
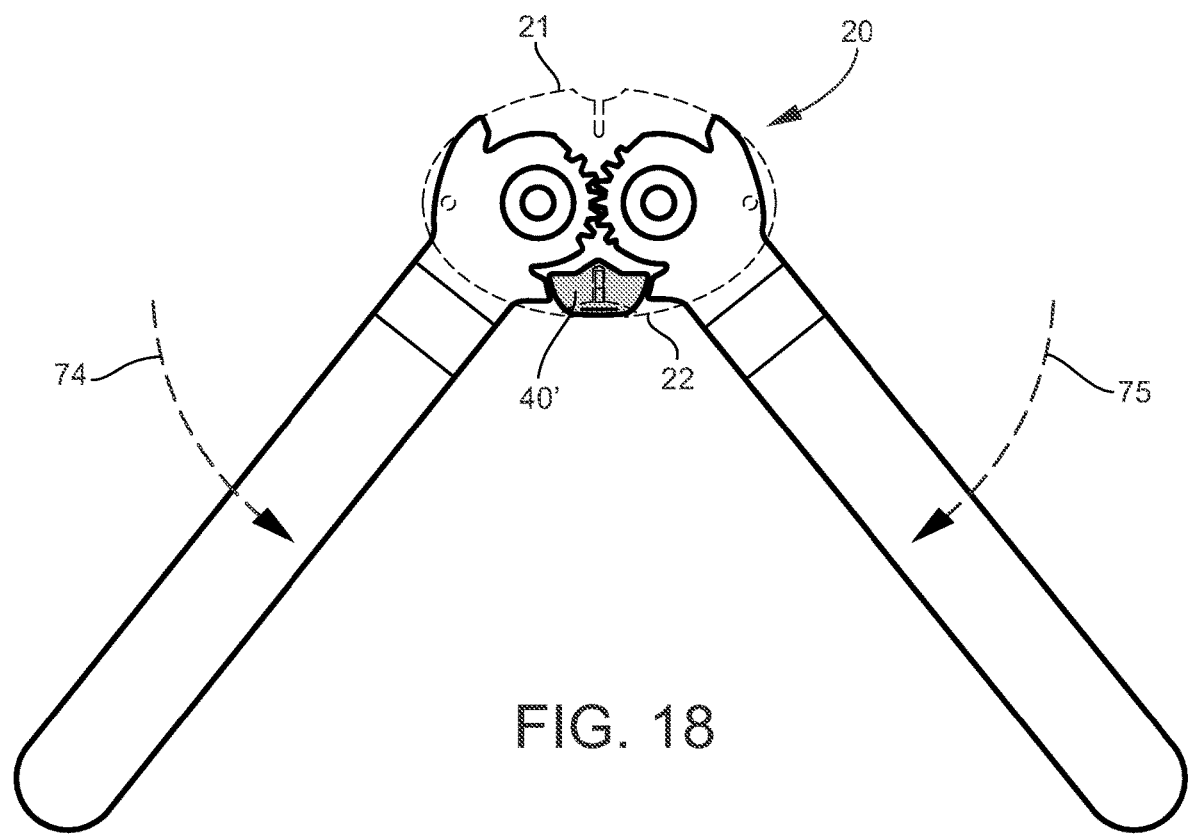
FIGS. 18 and 19 are views of the brace strut showing the smaller hinge stop positioned on the flexion side of the ROM hinge.
Figure 19:
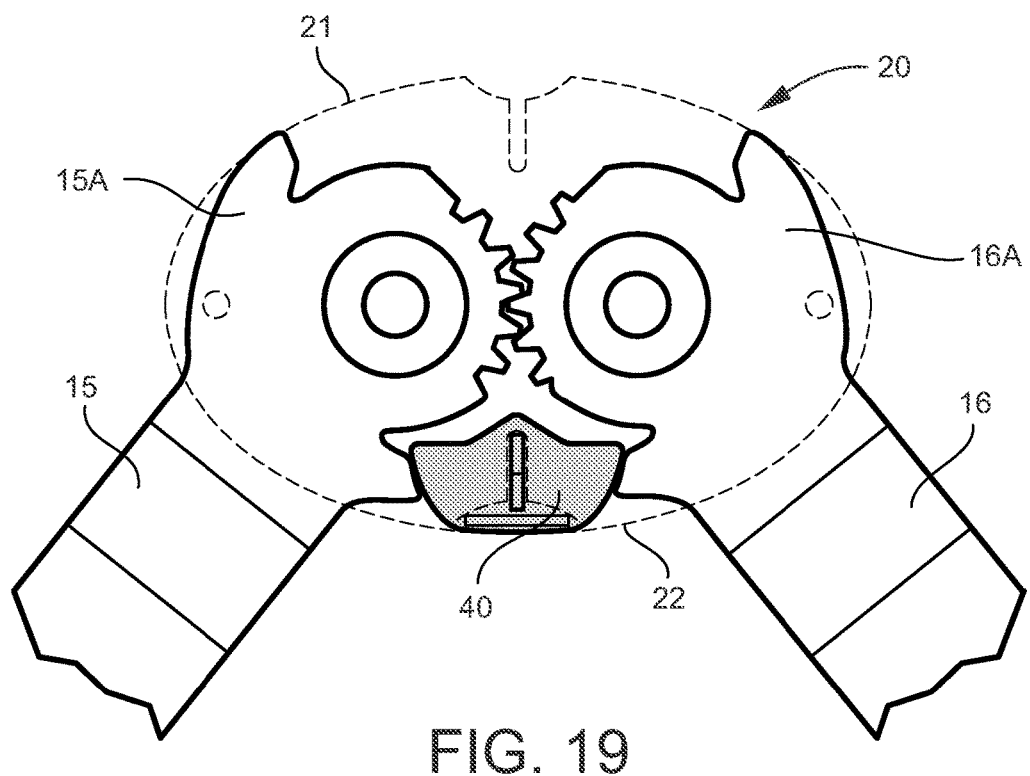

FIGS. 16 and 17 show a smaller hinge stop 40' located on the extension side 21 of ROM hinge 20 between proximal ends 15A, 16A of the hinge bars 15, 16. In this position, the hinge bars 15, 16 can freely pivot within a greater range of motion indicated by arrow 72. FIGS. 18 and 19 show the smaller hinge stop 40' inserted on the flexion side 22 of ROM hinge 20 between proximal ends 15A, 16A of the hinge bars 15, 16. In this position, the hinge bars 15, 16 can freely pivot within a range of motion indicated by arrows 74, 75.

Figure 20:
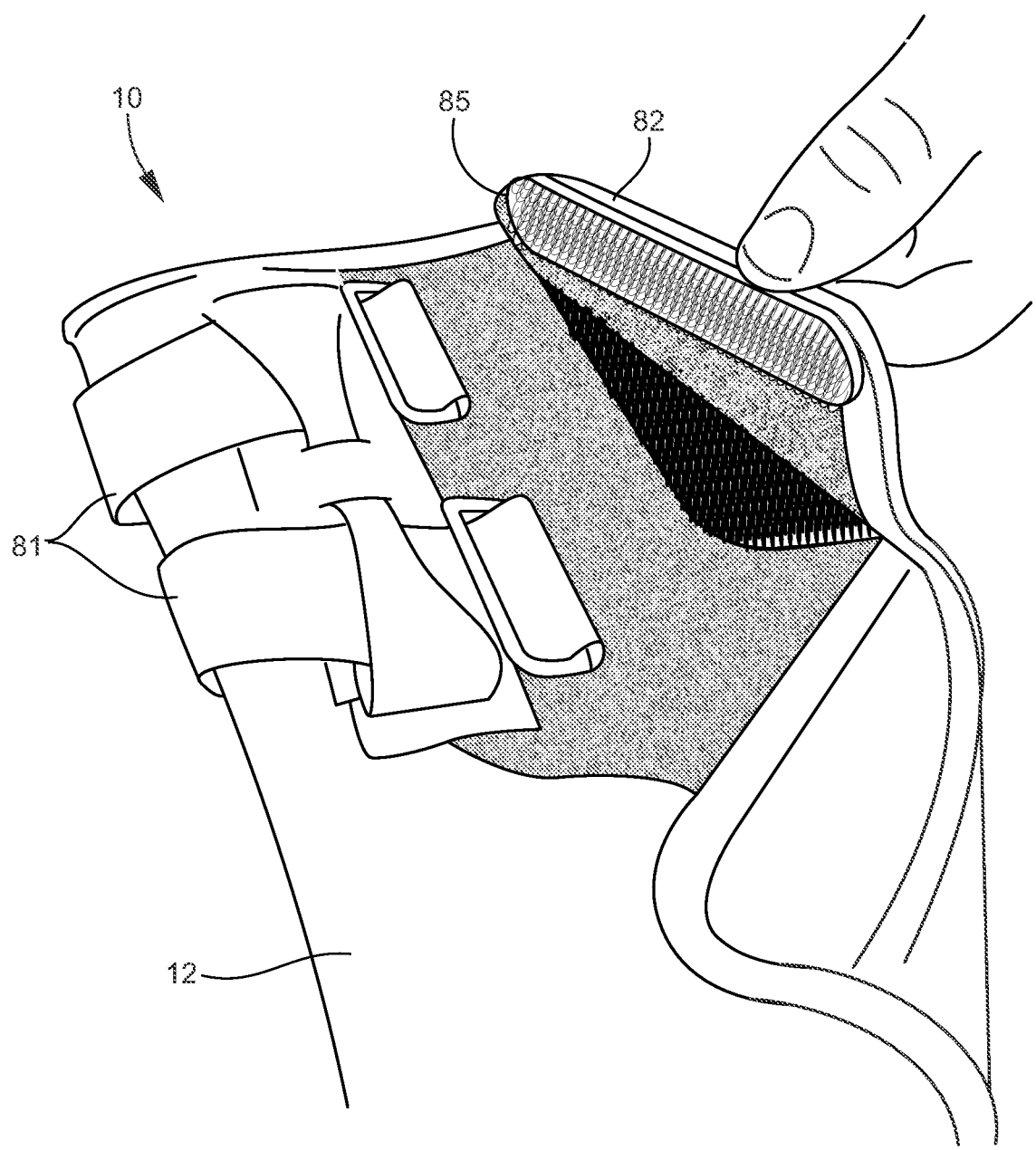
FIG. 20 is fragmentary perspective of the exemplary knee brace showing an edge fastener strip of the wraparound fabric body.

Referring to FIG. 20, in exemplary embodiments described above the knee brace 10 may be secured to the leg by a one-piece, flexible wraparound fabric body 12 having hook and loop fasteners and one or more flexible closure straps 81. Free edges 82 of the fabric body 12 may be closely and uniformly held to the fabric body 12 by strips of inside edge combination hook/loop fasteners 85 mating with complementary hook surfaces or loop surfaces or combination hook/loop surfaces, thereby limiting a tendency of the free edges 82 to turn upwardly and outwardly from the fabric body 12.

For the purposes of describing and defining the present invention it is noted that the use of relative terms, such as "substantially", "generally", "approximately", and the like, are utilized herein to represent an inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

Exemplary embodiments of the present invention are described above. No element, act, or instruction used in this description should be construed as important, necessary, critical, or essential to the invention unless explicitly described as such. Although only a few of the exemplary embodiments have been described in detail herein, those skilled in the art will readily appreciate that many modifications are possible in these exemplary embodiments without materially departing from the novel teachings and advantages of this invention. Accordingly, all such modifications are intended to be included within the scope of this invention as defined in the appended claims.

In the claims, any means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. Unless the exact language "means for" (performing a particular function or step) is recited in the claims, a construction under 35 U.S.C. § 112(f) [or 6th paragraph/pre-AIA] is not intended. Additionally, it is not intended that the scope of patent protection afforded the present invention be defined by reading into any claim a limitation found herein that does not explicitly appear in the claim itself.

What is claimed:

1. A brace adapted for being applied to a body part of a wearer, comprising:
   an elongated strut including first and second rigid hinge bars, each hinge bar having a proximal end and a distal end;
   an adjustable dual-axis range of motion (ROM) hinge pivotably interconnecting the proximal ends of said first and second rigid hinge bars at respective spaced apart pivot points, and having a flexion side and an extension side, said adjustable dual-axis ROM hinge comprising:
   a hinge plate residing adjacent the proximal ends of said first and second rigid hinge bars;
   first and second spaced apart pivot fasteners securing said hinge bars to said hinge plate at respective pivot points; and
   a resilient flex member;
   an exchangeable range-controlling hinge stop located on a selected one of the flexion and extension sides of said adjustable dual-axis ROM hinge adjacent the proximal ends of said first and second rigid hinge bars and between said hinge plate and said resilient flex member, and wherein said exchangeable range-controlling hinge stop is designed to engage said hinge bars at a predetermined flexion/extension limit, thereby restricting pivoting movement of said elongated strut and custom limiting a range of extension or flexion of the body part; and
   a stop retention post extending outwardly from a top planar surface of said hinge stop, and having a stair-step shape comprising integrally formed short and tall portions cooperating with said resilient flex member to hold said exchangeable range-controlling hinge stop in position relative to said first and second rigid hinge bars, and whereby lifting said resilient flex member outwardly away from said hinge plate allows said exchangeable range-controlling hinge stop to be removed from said adjustable dual-axis ROM hinge and exchanged.

2. The brace according to claim 1, wherein proximal ends of said first and second rigid hinge bars comprise a plurality of intermeshing gear teeth.

3. The brace according to claim 2, wherein proximal ends of said first and second rigid hinge bars further comprise respective stop surfaces adjacent leading ones of said plurality of gear teeth, said stop surfaces cooperating to restrict hyperextension of said elongated strut.

4. The brace according to claim 1, wherein said exchangeable range-controlling hinge stop is located on the extension side of said adjustable dual-axis ROM hinge and is configured to limit pivoting movement of said elongated strut, such that a range of extension of the body part is restricted at a selected extension angle between 10-degrees and 60-degrees.

5. The brace according to claim 1, wherein said exchangeable range-controlling hinge stop is located on the flexion side of said adjustable dual-axis ROM hinge and is configured to limit pivoting movement of said elongated strut, such that a range of flexion of the body part is restricted at a selected flexion angle between 10-degrees and 90-degrees.

6. The brace according to claim 1, and comprising a second hinge plate adjacent said resilient flex member, and cooperating with said hinge plate to sandwich the proximal ends of said hinge bars therebetween.

7. The brace according to claim 1, wherein said exchangeable range-controlling hinge stop comprises a surface fingernail groove designed to facilitate removal of said exchangeable range-controlling hinge stop from said adjustable dual-axis ROM hinge.

8. The brace according to claim 1, wherein the proximal ends of said first and second rigid hinge bars define respective stop notches, and wherein said exchangeable range-controlling hinge stop comprises opposing integrally formed end tongues designed to insert into respective stop notches at the predetermined flexion/extension limit.

9. A brace adapted for being applied to a body part of a wearer, comprising:
   an elongated strut extending between opposite ends of said brace and including first and second rigid hinge bars, each hinge bar having a proximal end and a distal end;
   an adjustable dual-axis range of motion (ROM) hinge pivotably interconnecting the proximal ends of said first and second rigid hinge bars at respective spaced apart pivot points, and having a flexion side and an extension side, said adjustable dual-axis ROM hinge comprising:
   a hinge plate residing adjacent the proximal ends of said first and second rigid hinge bars;
   first and second spaced apart pivot fasteners securing said hinge bars to said hinge plate at respective pivot points; and
   a flex member;
   an exchangeable range-controlling hinge stop located on a selected one of the flexion and extension sides of said adjustable dual-axis ROM hinge adjacent the proximal ends of said first and second rigid hinge bars and between said hinge plate and said flex member, and wherein said exchangeable range-controlling hinge stop is designed to engage said hinge bars at a predetermined flexion/extension limit, thereby restricting pivoting movement of said elongated strut and custom limiting a range of extension or flexion of the body part; and
   a stop retention post extending outwardly from a top planar surface of said hinge stop, and having a stair-step shape comprising integrally formed short and tall portions cooperating with said flex member to hold said exchangeable range-controlling hinge stop in position relative to said first and second rigid hinge bars, and whereby lifting said flex member outwardly away from said hinge plate allows said exchangeable range-controlling hinge stop to be removed from said adjustable dual-axis ROM hinge and exchanged; and
   a flexible strap closure adapted for securing and positioning said elongated strut on the body part of the wearer.

10. The brace according to claim 9, wherein proximal ends of said first and second rigid hinge bars comprise a plurality of intermeshing gear teeth.

11. The brace according to claim 10, wherein proximal ends of said first and second rigid hinge bars comprise respective stop surfaces directly adjacent leading ones of said plurality of gear teeth, said stop surfaces cooperating to restrict hyperextension of said first and second rigid hinge bars.

12. The brace according to claim 9, wherein exchangeable range-controlling hinge stop is located on the extension side of said adjustable dual-axis ROM hinge and is configured to limit pivoting movement of said first and second rigid hinge bars, such that a range of extension of the body part is restricted at a selected extension angle between 10-degrees and 60-degrees.

13. The brace according to claim 9, wherein said exchangeable range-controlling hinge stop is located on the flexion side of said adjustable dual-axis ROM hinge and is configured to limit pivoting movement of said first and second rigid hinge bars, such that a range of flexion of the body part is restricted at a selected flexion angle between 10-degrees and 90-degrees.

14. The brace according to claim 9, and comprising a second hinge plate adjacent said resilient flex member, and cooperating with said hinge plate to sandwich the proximal ends of said hinge bars therebetween.

15. The brace according to claim 9, wherein said exchangeable range-controlling hinge stop comprises a surface fingernail groove designed to facilitate removal of said exchangeable range-controlling hinge stop from said adjustable dual-axis ROM hinge.

16. The brace according to claim 9, wherein the proximal ends of said first and second rigid hinge bars define respective stop notches, and wherein said exchangeable range-controlling hinge stop comprises opposing integrally formed end tongues designed to insert into respective stop notches at the predetermined flexion/extension limit.

17. A brace adapted for being applied to a body part of a wearer, comprising:
   an elongated strut extending between opposite ends of said brace and including first and second rigid hinge bars, each hinge bar having a proximal end and a distal end;
   an adjustable dual-axis range of motion (ROM) hinge pivotably interconnecting the proximal ends of said first and second rigid hinge bars at respective spaced apart pivot points, and having a flexion side and an extension side, said adjustable dual-axis ROM hinge comprising:
      first and second hinge plates residing adjacent said first and second rigid hinge bars, and sandwiching the proximal ends of said hinge bars therebetween;
      first and second spaced apart pivot fasteners securing said first and second rigid hinge bars to said first and second hinge plates at respective pivot points; and
      a resilient flex ring affixed to an outside of said second hinge plate at opposite ends of said adjustable dual-axis ROM hinge and continuously unattached to said second hinge plate along the flexion and extension sides of said adjustable dual-axis ROM hinge;
      an exchangeable range-controlling hinge stop located on a selected one of the flexion and extension sides of said adjustable dual-axis ROM hinge adjacent the proximal ends of said first and second rigid hinge bars and between said first and second hinge plates, and wherein said exchangeable range-controlling hinge stop is designed to engage said hinge bars at a predetermined flexion/extension limit, thereby restricting pivoting movement of said elongated strut and custom limiting a range of extension or flexion of the body part, and said exchangeable range-controlling hinge stop comprising a stop retention post extending outwardly from a top planar surface of said hinge stop, and having a stair-step shape comprising integrally formed short and tall portions, said short portion having a height corresponding to a thickness of one of said first and second hinge plates, and said tall portion adapted for inserting into a selected complementary post hole formed in the peripheral margin of said resilient flex ring at the flexion or extension sides of said adjustable dual-axis ROM hinge, and said retention post cooperating with said resilient flex ring to hold said exchangeable range-controlling hinge stop in position relative to said first and second rigid hinge bars, and whereby lifting said resilient flex ring outwardly away from said second hinge plate allows said exchangeable range-controlling hinge stop to be removed from said adjustable dual-axis ROM hinge and exchanged; and
   a flexible strap closure adapted for securing and positioning said elongated strut on the body part of the wearer.

18. The brace according to claim 17, wherein said second hinge plate comprises an edge slot aligned with the post hole of said flex ring for receiving the retention post of said exchangeable range-controlling hinge stop.

\* \* \* \* \*